United States Patent
Jallon (10) Patent No.: US 12,313,530 B2
(45) Date of Patent: May 27, 2025

(54) METHOD FOR CALIBRATING A GAS SENSOR AND METHOD FOR MEASURING A GAS USING THE CALIBRATION

(71) Applicant: ELICHENS, Grenoble (FR)

(72) Inventor: Pierre Jallon, Grenoble (FR)

(73) Assignee: ELICHENS, Grenoble (FR)

(*) Notice: Subject to any disclaimer, the term of this patent is extended or adjusted under 35 U.S.C. 154(b) by 135 days.

(21) Appl. No.: 18/262,361

(22) PCT Filed: Jan. 19, 2022

(86) PCT No.: PCT/EP2022/051156
§ 371 (c)(1),
(2) Date: Jul. 20, 2023

(87) PCT Pub. No.: WO2022/157208
PCT Pub. Date: Jul. 28, 2022

(65) Prior Publication Data
US 2024/0085314 A1    Mar. 14, 2024

(30) Foreign Application Priority Data

Jan. 21, 2021 (FR) .................. FR2100597

(51) Int. Cl.
*G01N 21/31* (2006.01)
*G01N 33/00* (2006.01)

(52) U.S. Cl.
CPC ......... *G01N 21/31* (2013.01); *G01N 33/0006* (2013.01); *G01N 2201/127* (2013.01)

(58) Field of Classification Search
CPC .... G01J 3/28; G01J 3/427; G01N 2021/3137; G01N 21/274; G01N 21/31; G01N 21/314;
(Continued)

(56) References Cited

U.S. PATENT DOCUMENTS

| 5,026,992 A | 6/1991 | Wong |
| 11,041,801 B2 | 6/2021 | Mayoue et al. |

(Continued)

FOREIGN PATENT DOCUMENTS

| EP | 3179233 A1 | 6/2017 |
| EP | 3593119 B1 | 4/2021 |

(Continued)

OTHER PUBLICATIONS

International Search Report for International Application No. PCT/EP2022/051156, mailed May 3, 2022, 6 pages with English translation.

(Continued)

*Primary Examiner* — Hina F Ayub
(74) *Attorney, Agent, or Firm* — TraskBritt (57) ABSTRACT

In a method for calibrating a gas sensor—for determining a gaseous species concentration in a gas, which species absorbs light in an absorption spectral band—the gas sensor includes a chamber for containing the gas; a light source through which a supply electrical current is passable to raise the light source to a temperature; a measurement photodetector for measuring—in a measurement spectral band comprising the absorption spectral band—a measured intensity of a light beam emitted by the light source and transmitted by the gas in the chamber; and a reference photodetector for measuring a reference intensity of a reference light beam emitted by the light source in a reference spectral band. A non-linear calibration function is determined to estimate an intensity, measured in the measurement spectral band by the measurement photodetector in the absence of gaseous species, from a reference intensity measured in the reference spectral band.

12 Claims, 6 Drawing Sheets

(58) Field of Classification Search
CPC ......... G01N 21/3504; G01N 2201/127; G01N 33/0006
See application file for complete search history.

(56) References Cited

U.S. PATENT DOCUMENTS

2006/0262311 A1* 11/2006 Muta ..................... G01N 21/31
356/437
2013/0301052 A1    11/2013 MacGregor et al.
2018/0095028 A1*  4/2018 Jourdainne ........ G01N 21/3518

FOREIGN PATENT DOCUMENTS

WO    2007/064370  A2    6/2007
WO    2018/229239  A1    12/2018
WO    2019/145649  A1    8/2019

OTHER PUBLICATIONS

International Written Opinion for International Application No. PCT/EP2022/051156, mailed May 3, 2022, 10 pages with English machine translation.

* cited by examiner

METHOD FOR CALIBRATING A GAS SENSOR AND METHOD FOR MEASURING A GAS USING THE CALIBRATION

CROSS-REFERENCE TO RELATED APPLICATIONS

This application is a national phase entry under 35 U.S.C. § 371 of International Patent Application PCT/EP2022/051156, filed Jan. 19, 2022, designating the United States of America and published as International Patent Publication WO 2022/157208 A1 on Jul. 28, 2022, which claims the benefit under Article 8 of the Patent Cooperation Treaty to French Patent Application Serial No. FR2100597, filed Jan. 21, 2021.

TECHNICAL FIELD

The technical field of the disclosure is an optical method for analyzing a gas, using a light source of the black body or gray body type, and by measuring the absorption of a light beam emitted by the light source.

BACKGROUND

Recourse to optical methods for analyzing a gas is commonplace. Sensors are able to determine the composition of a gas on the basis that the species of which the gas is composed have different spectral absorption properties than one another. Thus, by knowing an absorption spectral band for a gaseous species, its concentration can be determined by estimating the absorption of the light passing through the gas, using the Beer-Lambert Law. This principle makes it possible to estimate the concentration of a gaseous species present in the gas.

According to the most current methods, the gas analyzed extends between a light source and a photodetector, referred to as measurement photodetector, the latter being intended to measure a light beam transmitted by the gas that is to be analyzed, the light beam being partially absorbed by this gas. The light source is usually a source emitted in the infrared, the method employed usually being referred to as NDIR detection where NDIR stands for nondispersive infrared. Such a principle has often been employed and is described, for example, in documents U.S. Pat. No. 5,026,992 or WO2007064370.

The usual methods generally involve measuring a light beam, referred to as reference light beam, emitted by the source, the reference light beam not being absorbed, or being absorbed only to a negligible extent, by the gas being analyzed. Measuring the reference light beam makes it possible to estimate the intensity of the light beam emitted by the source, or to estimate the light beam that would be detected by the measurement photodetector in the absence of absorption by the gas being analyzed. This technology is referred to as "double beam." Comparing the light beam in the presence of gas with the light beam without gas makes it possible to characterize the absorption of the gas. It involves, for example, determining a quantity of a gaseous species in the gas using the technology referred to as NDIR absorption spectroscopy. The reference light beam is measured by a reference photodetector. This may be a resonance photodetector different than the measurement photodetector and designed to be positioned facing the light source, the reference photodetector being associated with a reference optical filter. The reference optical filter defines a reference spectral band in which the gas that is to be analyzed exhibits no significant absorption.

The inventor has found that the use of a reference light beam for estimating the light beam that would be detected by the measurement photodetector in the absence of absorption by the gas being analyzed can prove to be a source of significant uncertainty. The inventor is proposing a method that allows this disadvantage to be overcome in such a way as to improve the precision of the measurement.

BRIEF SUMMARY

A first subject of the disclosure is a method for calibrating a gas sensor, the gas sensor being intended to determine a concentration of a gaseous species in a gas, the gaseous species being able to absorb light in an absorption spectral band, the gas sensor comprising:
 a chamber configured to contain the gas; and
 a light source, a measurement photodetector and a reference photodetector, the light source being configured to emit an incident light beam, the incident light beam traveling through the chamber toward the measurement photodetector and toward the reference photodetector;
the gas sensor being such that
the light source is configured to have a supply electric current passing through it so as to raise the light source to a temperature value;
the measurement photodetector is designed to measure an intensity, referred to as measurement intensity, of a light beam emitted by the light source, transmitted by the gas contained in the chamber, in a measurement spectral band comprising the absorption spectral band; and
the reference photodetector is designed to measure a reference intensity of a reference light beam emitted by the light source in a reference spectral band;
the method comprising the following steps:
 (i) incorporating a calibration function, that is preferably nonlinear, the calibration function making it possible to estimate an intensity, measured in the measurement spectral band by the measurement photodetector in the absence of gaseous species, from a reference intensity measured in the reference spectral band by the reference photodetector, the calibration function being dependent on parameters;
 (ii) filling the chamber with a gas containing a zero concentration, or concentration considered to be zero, of the gaseous species;
 (iii) having the measurement photodetector measure a measurement intensity in the measurement spectral band, and having the reference photodetector measure a reference intensity in the reference spectral band, step (iii) being repeated at various calibration instants with the source supply current being modified between different calibration instants; and
 (iv) from the measurements resulting from (iii), determining the parameters of the calibration function.

Step (i) may include incorporating a nonlinear parametric model of the calibration function. The parametric model is dependent on parameters that are determined during step (iv).

Step (iv) may comprise:
 iv-1) from each reference intensity measured at each respective calibration instant, estimating a measured intensity resulting from the measurement photodetector using the calibration function;

iv-2) for each supply current value, comparing the measured intensity estimated during iv-1) with the measured intensity measured by the measurement photodetector; and iv-3) determining the parameters of the calibration function that minimize the comparisons resulting from iv-2).

During step (iii), the supply current may vary between two extreme values corresponding respectively to −15% and +15% of a nominal supply current.

According to one embodiment, step (iii) is carried out by bringing the gas sensor to different values of an ambient temperature; and step (iv) is carried out incorporating the measurements resulting from (iii) for each temperature value so as to obtain a calibration function associated with each respective ambient temperature value.

According to one embodiment, step (iii) is carried out by bringing the gas sensor to different ambient temperature values; and step (iv) is carried out incorporating the measurements resulting from (iii) for all of the temperature values so as to obtain a calibration function that is common to all of the ambient temperature values.

According to one embodiment, one parameter of the calibration function forms an exponent applied to the reference intensity, the parameter being estimated during step (iv).

According to one embodiment, one parameter of the calibration function is a proportionality parameter defining proportionality between the estimated intensity in the measurement spectral band in the absence of gaseous species, and the reference intensity to which the exponent is applied, the proportionality parameter being estimated during step (iv).

According to one embodiment, the calibration function comprises a ratio of a numerator over a denominator, such that:

the numerator comprises a first multiplicative parameter applied to the reference intensity;

the denominator comprises a second multiplicative parameter applied to the reference intensity; and the first multiplicative parameter and the second multiplicative parameter are estimated during step (iv).

A second subject of the disclosure is a method for measuring a quantity of a gaseous species present in a gas, the gaseous species being able to absorb light in an absorption spectral band, the method comprising the following steps:

a) placing the gas between a light source and a measurement photodetector, the light source being configured to emit an incident light beam, the incident light beam traveling through the gas toward the measurement photodetector, a supply electric current being passed through the light source so as to raise the light source to a temperature value;

b) illuminating the gas using the light source;

c) having the measurement photodetector measure an intensity, referred to as measured intensity, of a light beam transmitted by the gas in a measurement spectral band comprising the absorption spectral band;

d) having a reference photodetector measure an intensity, referred to as reference intensity, of a reference light beam, the reference light beam being emitted by the light source in a reference spectral band;

steps b) to d) being carried out at a measurement instant, the method comprising, at each measurement instant:

e) from the reference intensity measured by the reference photodetector, incorporating a calibration function so as to estimate a light beam intensity that would be detected by the measurement photodetector in the measurement spectral band in the absence of gaseous species; and f) estimating a quantity of the gaseous species from the measured intensity measured during step c) of the intensity estimated during step e);

the method being characterized in that the calibration function is established during a calibration phase, the calibration phase being performed by implementing steps (i) to (iv) of a method according to the first subject of the disclosure.

The calibration function may be established in such a way that:

step (iii) is carried out by bringing the gas sensor to different ambient temperature values;

step (iv) is carried out incorporating the measurements resulting from (iii) for each temperature value so as to obtain a calibration function associated with each respective ambient temperature value; and step e) comprises:

incorporating an ambient temperature, around the gas sensor; and selecting the calibration function as a function of the ambient temperature.

A third subject of the disclosure is a gas sensor intended to determine a concentration of a gaseous species in a gas, the gaseous species being able to absorb light in an absorption spectral band, the sensor comprising:

a chamber configured to contain the gas; and a light source, a measurement photodetector and a reference photodetector, the light source being configured to emit an incident light beam, the incident light beam traveling through the chamber toward the measurement photodetector and toward the reference photodetector;

the gas sensor being such that:

an electric supply current passes through the light source so as to raise the light source to a temperature value;

the measurement photodetector is designed to measure an intensity, referred to as measurement intensity, of a light beam emitted by the light source, transmitted by the gas contained in the chamber, in a measurement spectral band comprising the ab sorption spectral band;

the reference photodetector is designed to measure a reference intensity of a reference light beam emitted by the light source in a reference spectral band; and the sensor comprises a processing unit, programmed to store a calibration function, that is preferably nonlinear, established by the first object of the disclosure and to apply the calibration function to the reference intensity measured by the measurement photodetector.

According to one embodiment, the gas sensor comprises a temperature sensor configured to measure an ambient temperature at the measurement instant, the processing unit being programmed to select the calibration function as a function of the ambient temperature from among a plurality of calibration functions respectively associated with different ambient temperatures.

Embodiments of the disclosure will be better understood from reading the description of the embodiments set out in the remainder of the description in connection with the figures listed below.

BRIEF DESCRIPTION OF THE DRAWINGS

FIG. 4A also shows an estimate of the intensity measured, in the measurement spectral band, at each calibration instant, as a function of the intensity measured in the reference spectral band by the reference photodetector.

FIG. 5A also shows the estimate of the intensity measured, in the measurement spectral band, at each calibration instant, as a function of the intensity measured in the reference spectral band.

DETAILED DESCRIPTION

Figure 1A:
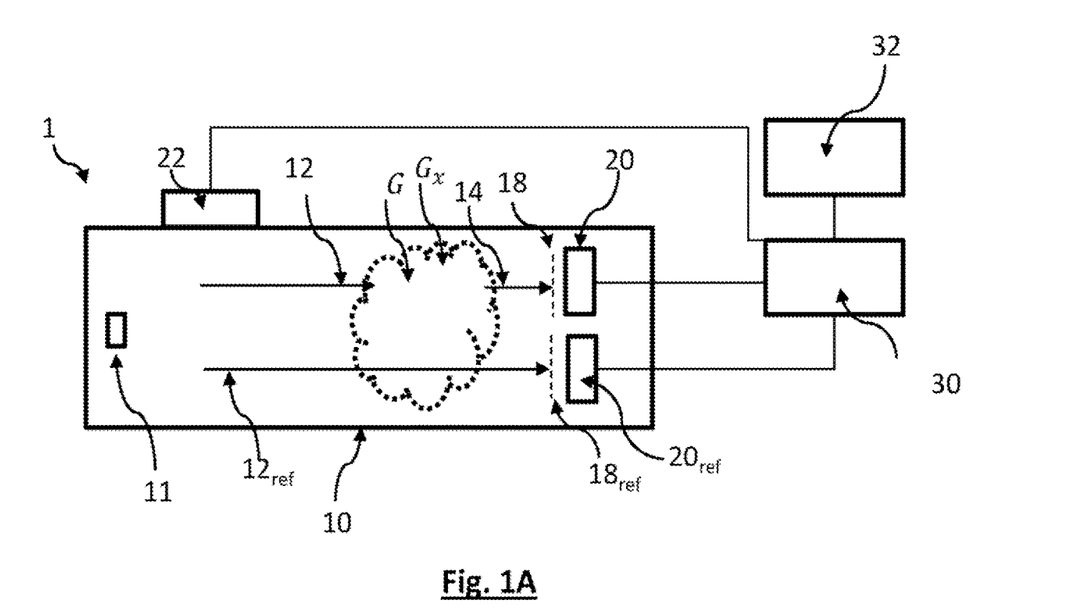
FIG. 1A depicts one example of a gas sensor that can be used for implementing embodiments of the disclosure.

FIG. 1A is one example of a sensor 1 for a gas G. The gas G comprises a gaseous species $G_x$ of which a quantity $c_x(t)$, for example a concentration, at a measurement instant t, is to be determined. This gaseous species absorbs a measurable proportion of the light in an absorption spectral band $\Delta_x$.

The gas sensor 1 comprises a chamber 10 defining an internal space inside which there are:
- a light source 11, able to emit a light beam 12, referred to as incident light beam, so as to illuminate a gas G extending in the internal space. The incident light beam 12 extends over an illumination spectral band $\Delta_{12}$;
- a photodetector 20, referred to as measurement photodetector, configured to detect a light beam 14 transmitted by the gas G, under the effect of the illumination of the latter by the incident light beam 12. The light beam 14 is designated by the term measurement light beam. It is detected, by the measurement photodetector 20, in a measurement spectral band $\Delta_{mes}$ defined as a function of the absorption spectral band $\Delta_x$ of the gaseous species $G_x$; and
- a reference photodetector $20_{ref}$, configured to detect a light beam $12_{ref}$, referred to as reference light beam in a reference spectral band $\Delta_{ref}$. The reference spectral band $\Delta_{ref}$ is a spectral band in which the absorption of the light beam 12 by the gas G can be considered to be negligible.

The reference spectral band $\Delta_{ref}$ is different than the measurement spectral band $\Delta_{mes}$.

The light source 11 is configured to emit the incident light beam 12 across the illumination spectral band $\Delta_{12}$, the latter being able to extend between the near ultraviolet and the mid infrared, for example between 200 nm and 10 µm, and usually between 1 µm and 10 µm. The absorption spectral band $\Delta_x$ for the gaseous species $G_x$ being analyzed is comprised within the illumination spectral band $\Delta_{12}$. The light source 11 may notably be a pulsed beam, the incident light beam 12 being a pulse of a duration generally comprised between 100 ms and 1 s. The light source 11 may notably be a light source of suspended filament type heated to a temperature comprised between 400° C. and 800° C. Its emission spectrum, in the illumination spectral band $\Delta_{12}$, corresponds to the emission spectrum of a black body.

The measurement photodetector 20 is preferably associated with an optical filter 18, defining the measurement spectral band $\Delta_{mes}$ that encompasses all or part of the absorption spectral band $\Delta_x$ of the gaseous species.

In the example considered, the measurement photodetector 20 is a thermopile, able to deliver a signal that is dependent on the intensity of the light beam detected. Alternatively, the measurement photodetector may be a photodiode or some other type of photodetector.

The reference photodetector $20_{ref}$ is placed next to the measurement photodetector 20 and is of the same kind thereas. It is associated with an optical filter, referred to as reference optical filter $18_{ref}$. The reference optical filter $18_{ref}$ defines the reference spectral band $\Delta_{ref}$ corresponding to a range of wavelengths that are not absorbed by the gaseous species considered. The reference passband $\Delta_{ref}$ is centered, for example, around the wavelength $\lambda_{ref}=3.91$ µm.

The intensity $I_{mes}(t)$ of the light beam 14 detected by the measurement photodetector 20 and referred to as measured intensity, at a measurement instant t, is dependent on the concentration $c_x(t)$ at the measurement instant, according to the Beer-Lambert relationship:

$$\text{abs}(t) = 1 - \frac{I_{mes}(t)}{I_0(t)} = 1 - e^{-att_{mes}c_x(t)} \quad (1)$$

where:
- $att_{mes}$ is a constant, which corresponds to the attenuation of the light beam in the spectral band $\Delta_{mes}$ in the chamber 10 for a unit concentration of the gaseous species $G_x$. This constant can be calculated on the basis of a plot of optical paths in the sensor, between the light source and the measurement photodetector, and of the absorption coefficient of the absorbing gas. It may also be determined by calibration;
- $c_x(t)$ is the concentration of the gaseous species $G_x$ at the instant t; and
- $I_0(t)$ is the intensity of the incident light beam, at the instant t, which corresponds to the intensity of the light beam, in the measurement spectral band $\Delta_{mes}$ that would reach the measurement photodetector 20 in the absence of absorbing gas in the chamber.

The comparison between $I_{mes}(t)$ and $I_0(t)$, which takes the form of a ratio $$\frac{I_{mes}(t)}{I_0(t)},$$

makes it possible to define an absorption abs(t) generated by the gaseous species considered at the instant t. As $att_{mes}$ is known, $c_x(t)$ can be determined.

Expression (1) assumes control of the intensity $I_0(t)$ of the incident light beam 12 at the measurement instant t.

Figure 1B:
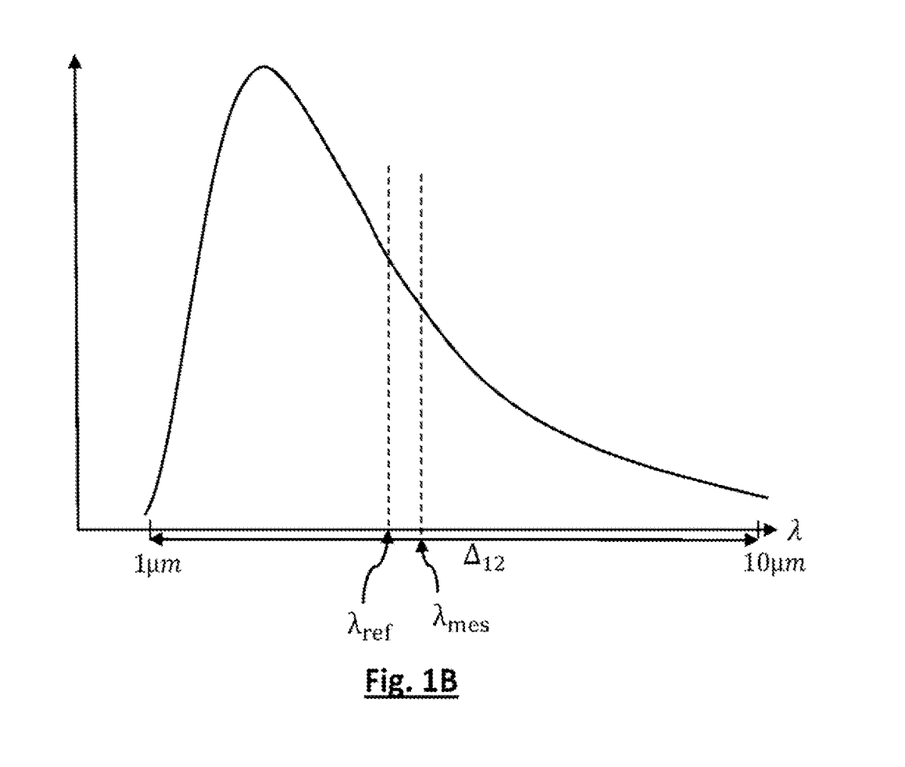
FIG. 1B schematically indicates an emission spectrum for a light source of black body type.

FIG. 1B indicates an emission spectrum for a light source 11 of the black body type, obeying Planck's law:

$$L(\lambda, T) = \frac{2hc^2}{\lambda^5} \frac{1}{e^{\frac{hc}{\lambda KT}} - 1} = \frac{2hc^2}{\lambda^5} \frac{1}{e^{\frac{\mu}{\lambda T}} - 1} \quad (2)$$

where
$L(\lambda,T)$ is the luminance, dependent on the wavelength $\lambda$ and on the surface temperature T of the black body;
h is Planck's constant;
K is the Boltzmann constant;
c is the speed of light in air; and $$-\mu = \frac{hc}{K}.$$

The emission spectrum S for the light source 11 corresponds to the change in luminance $L(\lambda,T)$ as a function of $\lambda$ when the light source is brought to a temperature T. In general, the temperature T is comprised between 400° C. and 800° C.

FIG. 1B indicates the illumination spectral band $\Delta_{12}$ for the light source 11, extending between 1 μm and 10 μm. The reference wavelength $\lambda_{ref}$ and the measurement wavelength $\lambda_{mes}$ have also been indicated, in broken line.

This type of light source is particularly advantageous because it allows the illumination spectrum S to be modulated simply by modulating the temperature T of the source. Thus, for each temperature T there is an associated illumination spectrum S.

It is known that the emissivity of a light source of the black body or gray body type can vary over time. The temporal variation in the emission of the light source 11 is taken into consideration by the reference photodetector $20_{ref}$. The latter is designed to detect a reference light beam $12_{ref}$, indicative of the incident light beam 12 emitted by the light source 11. The reference light beam $12_{ref}$ reaches the reference photodetector $20_{ref}$ without interacting with the gas G or without significantly interacting therewith.

The intensity of the reference light beam $12_{ref}$ detected by the reference photodetector $20_{ref}$ at the measurement instant t is referred to as the reference intensity $I_{ref}(t)$. From $I_{ref}(t)$ and knowing the emission spectrum of the light source 11 it is possible to infer the intensity $\hat{I}_0(t)$ of the light beam that would reach the measurement photodetector 20 in the absence of gas G. The reference intensity can be used to correct the measured intensity $I_{mes}(t)$ to account for rapid temporal fluctuations in power and the slow phenomenon of the aging of the light source 11.

The device comprises a microprocessor 30 connected to a memory 32 containing instructions for implementing the method steps described hereinbelow. The microprocessor 30 is configured to receive a signal indicative of the intensity $I_{ref}(t)$ of the reference light beam $12_{ref}$ measured by the reference photodetector $20_{ref}$ at each measurement instant t. The microprocessor 30 estimates the intensity $\hat{I}_0(t)$ from $I_{ref}(t)$.

From $I_{mes}(t)$ it is possible to estimate the absorption of the incident light beam using the expression:

$$\text{abs}(t) = 1 - \frac{I_{mes}(t)}{\hat{I}_0(t)}. \quad (3)$$

Using expression (1), $c_x(t)$ can then be obtained so that:

$$c_x(t) = -\frac{1}{att_{mes}} \ln\left(\frac{I_{mes}(t)}{\hat{I}_0(t)}\right) \quad (4)$$

It is usually considered that the ratio between the emissivity of the light source 11, respectively in the reference spectral band $\Delta_{ref}$ and in the measurement spectral band $\Delta_{mes}$ is constant. With such a hypothesis, the intensity $\hat{I}_0(t)$ is simply estimated from $I_{ref}(t)$ on the assumption that the theoretical emission spectrum of the light source is constant (i.e., that the temperature T is constant). Using (2) gives $\hat{I}_0(t) \propto I_{ref}(t)$, where $\propto$ refers to the "is proportional to" operator.

Figure 2A:
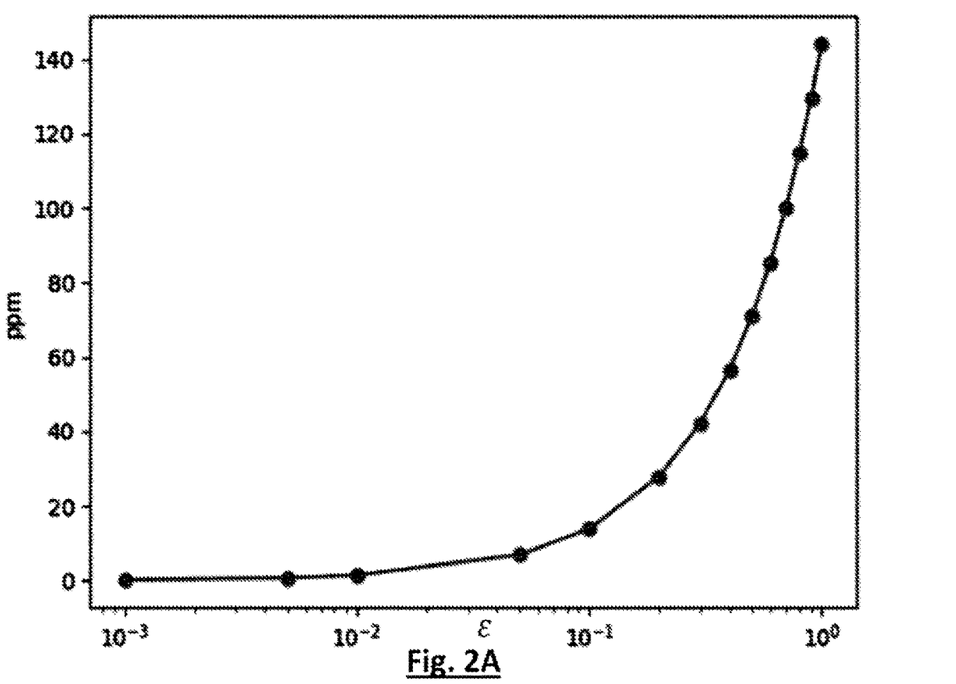
FIGS. 2A and 2B, respectively, depict an error in the measurement of the concentration of $CO_2$ and of $CH_4$ as a function of an error in the estimation of the light beam reaching the measurement photodetector.
Figure 2B:
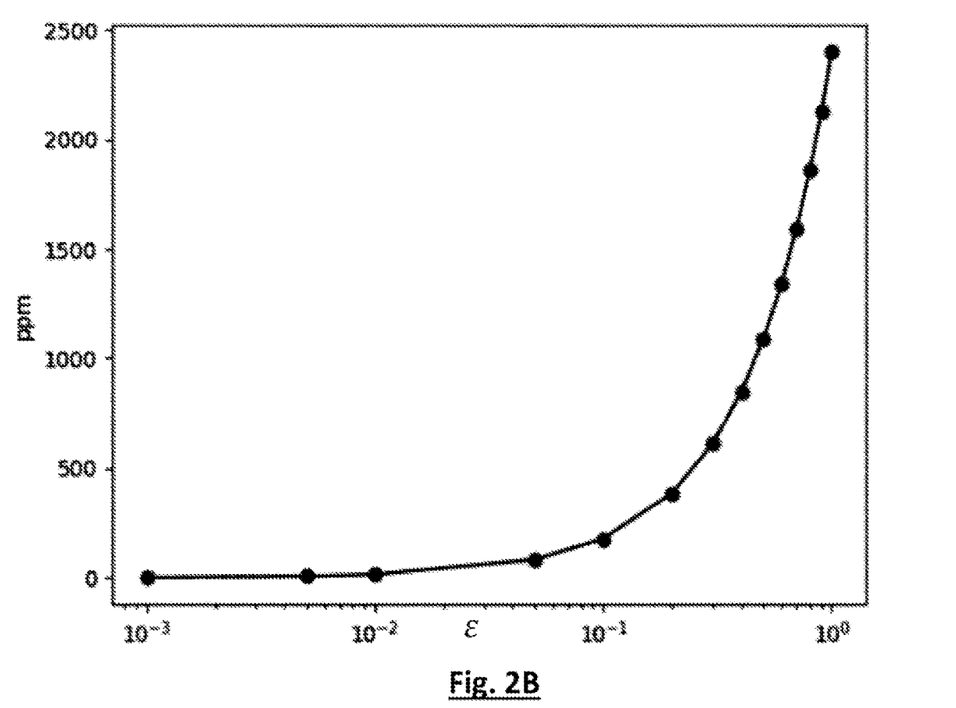

However, the inventor has found that by using expression (4), a small error ε in the estimate of $\hat{I}_0$ leads to a high error in the estimate $c_x$. FIGS. 2A and 2B indicate the uncertainty associated with $c_x$:
when $\lambda_{ref}$=3.91 μm and when $\lambda_{mes,x}$=4.26 μm, which corresponds to the absorption wavelength for $CO_2$: cf. FIG. 2A; and
when $\lambda_{ref}$=3.91 μm and when $\lambda_{mes,x}$=3.25 μm, which corresponds to the absorption wavelength for $CH_4$: cf. FIG. 2B.

In FIGS. 2A and 2B, the ordinate axis indicates an error associated with the concentration of $c_x$ (in units of ppm) and the abscissa axis corresponds to the error ε. For $CO_2$ (FIG. 2A), errors ε of 0.1 and 0.2 lead, respectively, to a measurement error of 14 ppm and 28 ppm. For $CH_4$ (FIG. 2B), errors ε of 0.1 and 0.2 lead, respectively, to a measurement error of 100 ppm and 450 ppm. The measurement errors calculated for $CO_2$ and $CH_4$ for the one same error in the estimation of $\hat{I}_0$ differ because the gradient of the curve indicated in FIG. 1B is different on the one hand between 3.91 μm and 4.26 μm and between 3.91 μm and 3.25 μm on the other hand. In addition, the absorptivity coefficients for the gases $CO_2$ and $CH_4$ are different.

Considering (2), $I_{ref}(t)$ and $I_0(t)$ can, for each instant t, be expressed as:

$$I_{ref}(t) = \frac{a_{ref} I(t)}{e^{\left(\frac{\mu}{\lambda_{ref} T(t)}\right)} - 1} \quad \text{and} \quad (6)$$

$$I_o(t) = \frac{a I(t)}{e^{\left(\frac{\mu}{\lambda_{mes,x} T(t)}\right)} - 1} \quad (7)$$

where:
I(t) is the light intensity radiated by the light source at the instant t;
T(t) is the temperature of the light source at the instant t;
$a_{ref}$ and a are dependent on the relative arrangements of the light source and of the measurement and reference photodetectors; and
μ is a constant defined in connection with expression (2).

The source temperature T is an important quantity because according to (2) it governs the emission spectrum of the light source, as indicated in FIG. 1B. The estimate of $\hat{I}_0$ from $I_{ref}$ is dependent on the emission spectrum of the light source 11 and therefore on the temperature T.

One important aspect of embodiments of the disclosure is to define a calibration function $f$ that makes it possible, from a measurement of $I_{ref}$ in the reference spectral band $\Delta_{ref}$, to make a precise estimate $\hat{I}_0$ of $I_0$ in the measurement spectral band $\Delta_{mes}$. It is important for the estimate $\hat{I}_0$ to be able to be robust with regard to variations in the temperature T of the light source.

Figure 3:
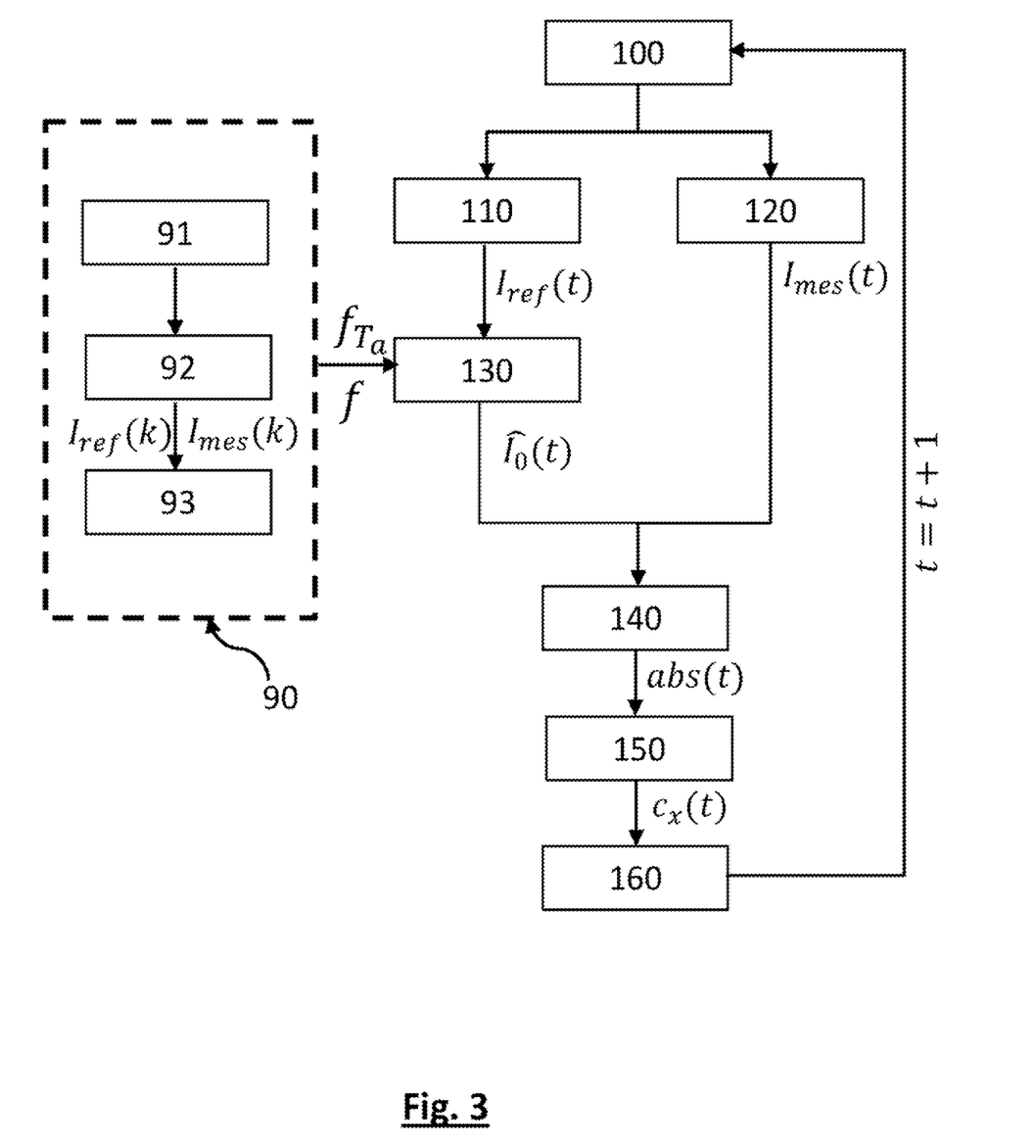
FIG. 3 indicates the main steps in a method for calibrating and using a gas sensor.

FIG. 3 indicates the main steps in implementing embodiments of the disclosure. During a calibration phase 90, the calibration function is defined. The calibration phase comprises steps 91 to 93. The calibration function resulting from the calibration phase is then used during a phase of using the gas sensor: steps 100 to 160.

The calibration phase 90 will be described first of all. The calibration phase is carried out during a plurality of calibration instants k.

Step 91: Incorporation of a Parametric Analytical Model of the Calibration Function $f$ During this step, an analytical model of the calibration function is defined. The analytical model is defined by one or more parameters θ. The quantity θ corresponds to the parameter of the model or to all of the parameters of the model.

A simple first analytical model is a proportional model. The calibration function $f$ is such that:

$$\hat{I}_0 = f(I_{ref}) = Z I_{ref} \tag{8}$$

Z is a positive real coefficient. According to this model, θ=Z.

A more refined, second analytical model is obtained by assuming that:
- the power of the source I(k) is constant but the temperature T(k) varies, leading to a variation in $I_{ref}(k)$;
- the term $$e^{\left(\frac{\mu}{\lambda_{ref} T(t)}\right)}$$

is large by comparison with 1.

This model is:

$$\hat{I}_0 = f(I_{ref}) = Z(I_{ref})^{\alpha} \tag{9}$$

where Z and α are positive real numbers.

This model comes from simplifying equations (6) and (7) whereby:

$$I_{ref}(k) = \frac{a_{ref} I(k)}{e^{\left(\frac{\mu}{\lambda_{ref} T(k)}\right)} - 1} \simeq \frac{a_{ref} I(k)}{e^{\left(\frac{\mu}{\lambda_{ref} T(k)}\right)}}.$$

which gives:

$$\frac{1}{T(k)} = \frac{\lambda_{ref}}{\mu} \ln\left(\frac{a_{ref} I(k)}{I_{ref}(k)}\right) \tag{10}$$

And likewise:

$$I_o(k) = \frac{a I(k)}{e^{\left(\frac{\mu}{\lambda_{mes} T(k)}\right)} - 1} \simeq \frac{a I(k)}{e^{\left(\frac{\mu}{\lambda_{mes} T(k)}\right)}} \tag{11}$$

Combining (10) with (11) gives:

$$I_o(k) = \frac{a I(k)}{\exp\left(\frac{\mu}{\lambda_{mes}} \frac{\lambda_{ref}}{\mu} \ln\left(\frac{a_{ref} I(k)}{I_{ref}(k)}\right)\right)} = Z(I_{ref}(k))^{\frac{\lambda_{ref}}{\lambda_{mes}}} = Z(I_{ref}(k))^{\alpha} \tag{12}$$

According to the model for expression (9), θ=(Z, α), α may be predetermined or determined during the course of calibration.

A third analytical model may be:

$$\hat{I}_0 = f(I_{ref}) = \frac{Z(1 + \xi(I_{ref}(k) - I_{ref}(k=0)))}{\left(1 + \sigma \frac{(1 + \xi(I_{ref}(k) - I_{ref}(k=0)))}{I_{ref}(k)}\right)^{\gamma} - 1} \tag{13}$$

The third analytical model is obtained by considering the quantities:

$$\tilde{I}_0(k) = \frac{I_0(k)}{I_0(k=0)}; \tag{14}$$

$$\tilde{I}_{ref}(k) = \frac{I_{ref}(k)}{I_{ref}(k=0)}; \text{ and} \tag{15}$$

$$\tilde{I}(k) = \frac{I(k)}{I(k=0)} \tag{16}$$

k=0 designates an arbitrarily selected reference instant. In general, the instant selected will be an instant at which the source is powered with its nominal voltage.

From (10), (15) and (16), $$\tilde{I}_{ref}(k) = \tilde{I}(k) \frac{e^{\left(\frac{\mu}{\lambda_{ref} T(k=0)}\right)} - 1}{e^{\left(\frac{\mu}{\lambda_{ref} T(k)}\right)} - 1} \tag{17}$$

From (17), T(k) can be expressed as:

$$T(k) = \frac{\mu}{\lambda_{ref}} \cdot \frac{1}{\ln\left(1 + \sigma \frac{\tilde{I}(k)}{\tilde{I}_{ref}(k)}\right)} \tag{18}$$

where $$\sigma = I_{ref}(k=0)\left(e^{\left(\frac{\mu}{\lambda_{ref} T(k=0)}\right)} - 1\right) \tag{19}$$

From (11), (14) and (16)

$$\tilde{I}_0(k) = \tilde{I}(k) \frac{\left(e^{\left(\frac{\mu}{\lambda_{mes} T(k=0)}\right)} - 1\right)}{\left(e^{\left(\frac{\mu}{\lambda_{mes} T(k)}\right)} - 1\right)} \tag{20}$$

Using (18), gives:

$$\hat{I}_0(k) = \frac{Z\tilde{I}(k)}{\left(1 + \sigma \frac{\tilde{I}(k)}{I_{ref}(k)}\right)^{\frac{\lambda_{ref}}{\lambda_{mes}}} - 1} \quad (21)$$

Considering that the light intensity emitted by the light source varies only a little, the term $\tilde{I}(k)$ can be linearized using the expression:

$$\tilde{I}(k) = 1 + \xi(I_{ref}(k) - I_{ref}(k=0)) \quad (22)$$

Combining (21) and (22) gives:

$$\hat{I}_0(k) = \frac{Z(1 + \xi(I_{ref}(k) - I_{ref}(k=0)))}{\left(1 + \sigma \frac{1 + \xi(I_{ref}(k) - I_{ref}(k=0))}{I_{ref}(k)}\right)^{\frac{\lambda_{ref}}{\lambda_{mes}}} - 1} \quad (23)$$

In order to account for the width of the spectral bands extending respectively about wavelengths $\lambda_{ref}$ and $\lambda_{mes}$, expression (23) can be generalized to:

$$\hat{I}_0(k) = \frac{Z(1 + \xi(I_{ref}(k) - I_{ref}(k=0)))}{\left(1 + \sigma \frac{1 + \xi(I_{ref}(k) - I_{ref}(k=0))}{I_{ref}(k)}\right)^{\gamma} - 1} \quad (24)$$

According to the model for the expressions (13) or (24), $\theta = (Z, \gamma, \alpha)$ or $\theta = (Z, \xi, \sigma)$ when considering the model resulting from expression (23). $Z, \gamma, \xi, \sigma$ are positive real numbers.

A fourth model is such that:

$$\hat{I}_0(k) = f(I_{ref}(k)) = \frac{ZI_{ref}(k)}{1 + \beta(I_{ref}(k) - I_{ref}(k=0))} \quad (25)$$

According to this model $\theta = (Z, \beta)$

Step 92: Calibration Measurements

During this step, the gas sensor is exposed to a gas that does not contain the gaseous species $G_x$ or contains it in negligible quantity. Thus, during each measurement, $I_{mes}(k) = I_0(k)$. Measurements of $I_{ref}(k)$ and of $I_{mes}(k)$ are carried out at different calibration instants k.

Between different calibration instants, the supply current supplied to the light source 11 is modified. The voltage across the terminals of the light source 11 is thus modified. This allows the light source to be raised to different temperature levels. For the one same value of current, different measurements of $I_{mes}(k)$ and $I_{ref}(k)$ are taken.

In general, the light source is associated with a nominal current value, whether this be defined in terms of current intensity or voltage. As a preference, during calibration, the supply current varies between two extreme values respectively comprised between −15% and +15% of the nominal value.

Step 93: Estimating the Parameters $\theta$

From the calibration measurements $I_{mes}(k)$ and $I_{ref}(k)$, the parameters of the parametric model are estimated by minimizing a performance index that represents a differential between:

each measured intensity $I_{mes}(k)$, which is equal to $I_0(k)$; and each intensity estimate $\hat{I}_0(k)$ from $I_{ref}(k)$ from the calibration function $f$: $\hat{I}_0(k) = f(I_{ref}(k))$.

Thus, $$\hat{\theta} = \underset{k}{\operatorname{argmin}} \sum_k [I_{mes}(k) - \hat{I}_0(k)]^2 \quad (30)$$

$\hat{\theta}$ is the estimate of the parameters $\theta$.

Figure 4A:
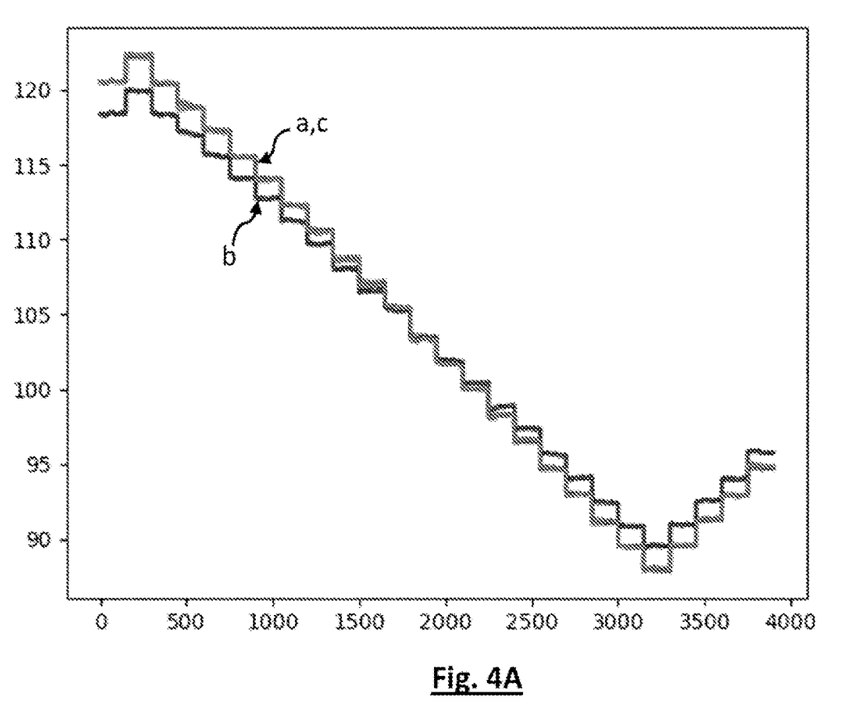
FIG. 4A indicates measurements, taken during a calibration, of an intensity of a light beam reaching the measurement photodetector, in the measurement spectral band, at different calibration instants.

FIG. 4A indicates the result of calibration measurements taken on a sensor from twenty-one different light source power supply current values. The supply current values were varied between two extreme values corresponding respectively to −15% and +15% of the nominal current value for the light source. The sensor was as described in EP3593119. 4000 measurements were taken at one measurement per second, the gaseous species measured being $CO_2$. At each calibration instant k, measurements of $I_{mes}(k)$ and $I_{ref}(k)$ were taken. From all of the measured values, the parameters $\theta$ of a calibration function were estimated by considering the parametric models respectively explained in expressions (8), (9), (23) and (25). FIG. 4A shows, as a function of time (abscissa axis, the units being seconds):

the measurement of $I_{mes}(k)$, in the knowledge that $I_{mes}(k) = I_0(k)$: curve a;

an estimate of $\hat{I}_0(k) = f(I_{ref}(k))$, according to expression (8): curve b; and an estimate of $\hat{I}_0(k) = f(I_{ref}(k))$, according to expression (25): curve c.

In FIG. 4A the abscissa axis corresponds to the calibration instants k with the units in seconds. The ordinate axis corresponds to $I_0(k)$ or $\hat{I}_0(k)$, the units being mV.

Figure 4B:
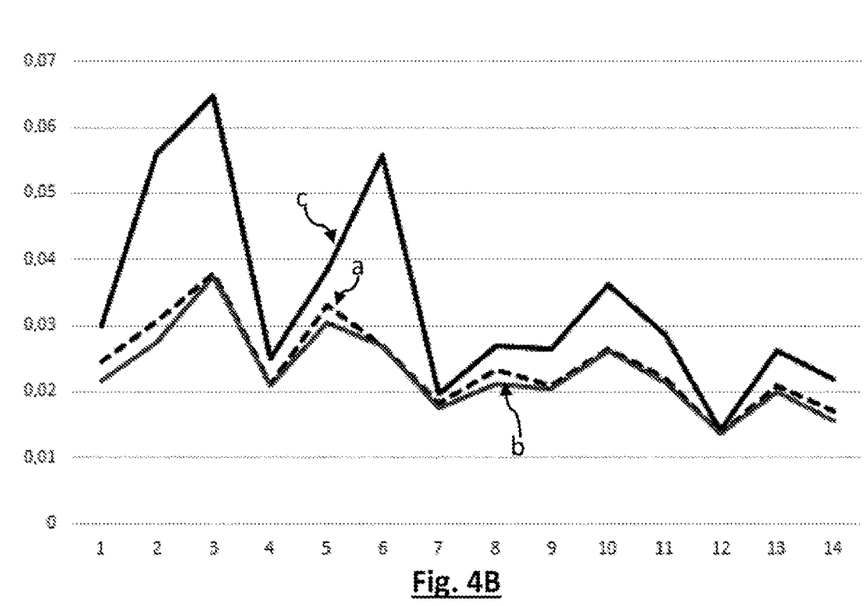
FIG. 4B shows the mean squared errors between estimates and measurements of the intensity of the light beam reaching the measurement sensor, incorporating different calibration functions, for different gas sensors.

A calibration as described in connection with FIG. 4A was carried out on 14 different sensors. FIG. 4B indicates, for each sensor (abscissa axis) a mean squared error (MSE on the ordinate axis), the MSE being obtained using the expression:

$$MSE = \frac{1}{N_k} \sum_k |I_{mes}(k) - \hat{I}_0(k)|^2 \quad (31)$$

In FIG. 4B, curves a and b respectively correspond to the parametric models established with expressions (9) and (23), respectively. Curve c) corresponds to a pre-established linear model (equation (8)) with Z=1.11977. It can be seen that models a) and b) appear to be particularly relevant.

A new calibration was performed by reducing the variation in light source supply current. The supply current values were varied between two extreme values corresponding respectively to 5% and +5% of the nominal light source current value. In this interval, 7 different light source supply current values were considered.

Figure 5A:
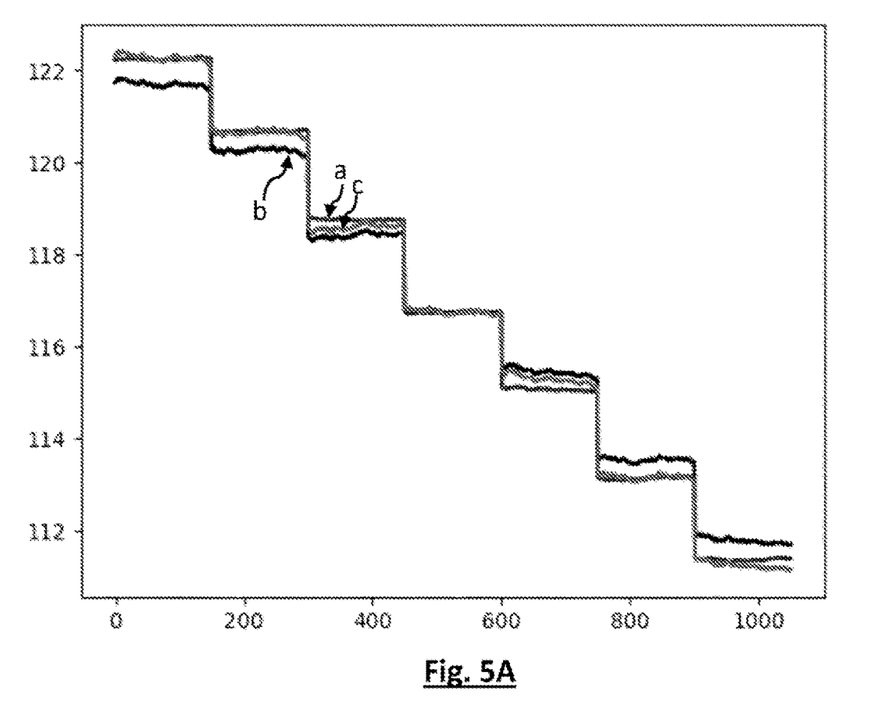
FIG. 5A indicates measurements, taken during calibration, of an intensity of a light beam reaching the image sensor in the measurement spectral band at different calibration instants.

1050 measurements were taken at one measurement per second. At each calibration instant k, measurements of $I_{mes}(k)$ and $I_{ref}(k)$ were taken. From all of the measured values the parameters $\theta$ of a calibration function were estimated by considering the parametric models respectively explained in expressions (8), (9), (23) and (25). FIG. 5A shows, as a function of time (abscissa axis—units in seconds):

the measurement of $I_{mes}(k)$, in the knowledge that $I_{mes}(k)=I_0(k)$: curve a;

an estimate of $\hat{I}_0(k)=f(I_{ref}(k))$, according to expression (8): curve b; and an estimate of $\hat{I}_0(k)=f(I_{ref}(k))$, according to expression (25): curve c.

In FIG. 5A, the abscissa axis corresponds to the calibration instants k with the units being seconds. The ordinate axis corresponds to $I_0(k)$ or $\hat{I}_0(k)$ with the units being mV.

Figure 5B:
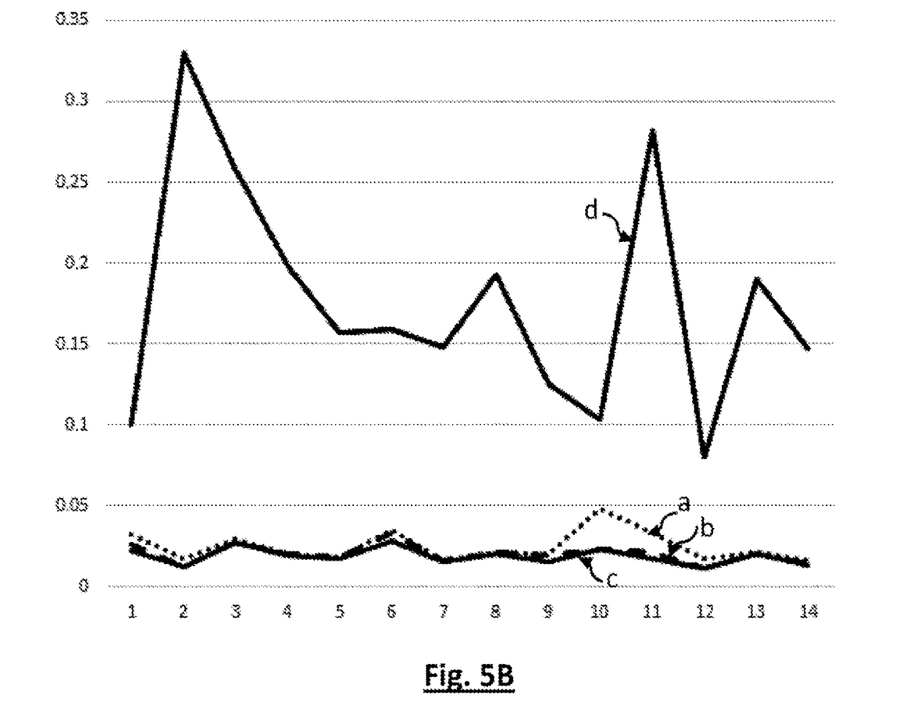
FIG. 5B shows mean squared errors between estimates and measurements of the intensity of the light beam reaching the measurement sensor, incorporating different calibration functions, for different gas sensors.

A calibration as described in connection with FIG. 5A was carried out on 14 different sensors. FIG. 5B indicates, on for each sensor (abscissa axis), a mean squared error (MSE on ordinate axis), the MSE being obtained according to expression (31). In FIG. 5B, curves a, b and c respectively correspond to the parametric models established according to expressions (8), (9), (23), respectively. Curve d corresponds to a pre-established linear model (equation (8)), with Z=1.11977. It may be seen that models b) and c) appear to be particularly relevant.

A use of a gas sensor by using a calibration function as described hereinabove will now be described in connection with FIG. 3.

Step 100: illumination of the gas at a measurement instant t;

Step 110: measurement of the reference intensity $I_{ref}(t)$ in the reference spectral band $\Delta_{ref}$ by the reference photodetector 20$_{ref}$.

Step 120: measurement of the intensity I(t) of the radiation 14 transmitted by the gas, in the measurement spectral band $\Delta_{mes}$, by the measurement photodetector 20.

Step 130: estimation of an intensity $\hat{I}_0(t)$ that would be detected by the measurement photodetector 14 in the measurement spectral band $\Delta_{20}$ in the absence of gas in the chamber. The estimate is carried out by incorporating the calibration function $f$ and applying the expression:

$$\hat{I}_0(t)=f(I_{ref}(t)).$$

Step 140: estimation of an absorption $$\text{abs}(k) = 1 - \frac{I(t)}{\hat{I}_0(t)}$$

in the measurement spectral band $\Delta_{mes}$.

Step 150: from the absorption, estimation of a quantity $c_x(k)$ of a gaseous species $G_x$ from the ratio applying expression (1).

Step 160: reiteration of steps 100 to 150, incrementing the measurement instant t or exiting the algorithm.

Figure 6A:
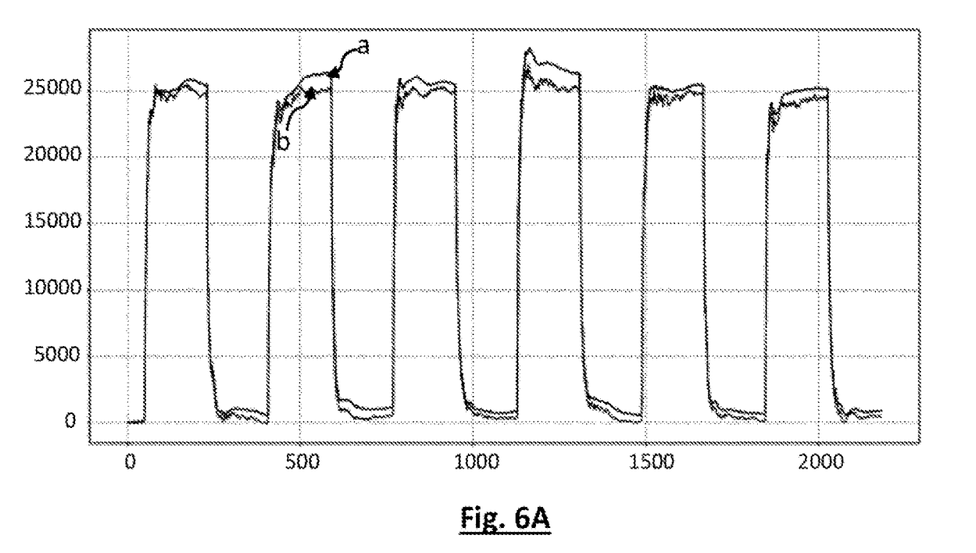
FIGS. 6A and 6B show examples of tests on a sensor with or without implementing embodiments of the disclosure.
Figure 6B:
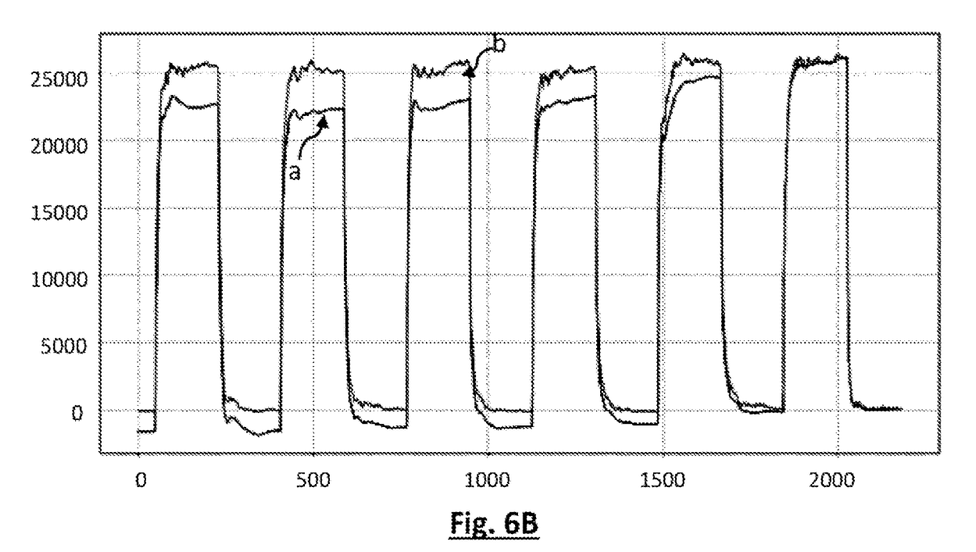

Gas sensors as described hereinabove were used by exposing them to a concentration of $CH_4$ that alternated between 25 000 ppm and 0 ppm. FIGS. 6A and 6B indicate the concentrations measured by each sensor, as a function of time, without implementing embodiments of the disclosure (curves a) and implementing embodiments of the disclosure (curves b), the calibration function being of the type $f(I_{ref}(k))=(Z(I_{ref}(k))^{\alpha}$ where $\alpha=1.12$. In FIGS. 6A and 6B, the abscissa axis corresponds to time (units in seconds) and the ordinate axis corresponds to the concentration measured by the sensor. It is found that embodiments of the disclosure (curves b) are able to approximate more closely to the exact values (25 000 ppm or 0 ppm) by comparison with the sensor used without implementing embodiments of the disclosure (curves a).

According to a variant, a gas sensor is associated with a temperature sensor 22. During the establishing of the calibration function $f$, an ambient temperature $T_a$ is measured for each calibration measurement. A calibration function $f_{Ta}$ is established for each ambient temperature. Alternatively, the one same calibration function $f$ is established accounting for the measurements taken for all of the ambient temperatures.

During measurements, a measurement of the ambient temperature of the sensor $T_a(t)$ is measured at each measurement instant t. The calibration function $f_{Ta}$ used is the one for which the ambient temperature is closest to the ambient temperature measured.

The invention claimed is:

1. A method for calibrating a gas sensor, the gas sensor being intended to determine a concentration of a gaseous species in a gas, the gaseous species absorbing light in an absorption spectral band, the gas sensor comprising:
   a chamber configured to contain the gas;
   a light source, a measurement photodetector and a reference photodetector, the light source being configured to emit an incident light beam, the incident light beam traveling through the chamber toward the measurement photodetector and toward the reference photodetector;
   wherein
      the light source is configured to have a supply electric current passing through it so as to raise the light source to a temperature value;
      the measurement photodetector is designed to measure a measurement intensity of a light beam emitted by the light source and transmitted by the gas contained in the chamber, in a measurement spectral band comprising the absorption spectral band;
      the reference photodetector is designed to measure a reference intensity of a reference light beam emitted by the light source in a reference spectral band;
   wherein the method comprises:
      (i) incorporating a calibration function that is nonlinear, the calibration function making it possible to estimate an intensity measured in the measurement spectral band by the measurement photodetector in the absence of gaseous species, from a reference intensity measured in the reference spectral band by the reference photodetector, the calibration function being dependent on parameters;
      (ii) filling the chamber with a gas containing a zero concentration, or concentration considered to be zero, of the gaseous species;
      (iii) having the measurement photodetector measure a measurement intensity in the measurement spectral band, and having the reference photodetector measure a reference intensity in the reference spectral band, step (iii) being repeated at various calibration instants with the source supply current being modified between the different calibration instants;
      (iv) from the measurements resulting from (iii), determining the parameters of the calibration function.

2. The method as claimed in claim 1, wherein step (iv) includes:
   iv-1) from each reference intensity measured at each respective calibration instant, estimating a measured intensity resulting from the measurement photodetector using the calibration function;
   iv-2) for each supply current value, comparing the measured intensity estimated during iv-1) with the measured intensity measured by the measurement photodetector;
   iv-3) determining the parameters of the calibration function that minimize the comparisons resulting from iv-2).

3. The method of claim 1, wherein during step (iii), the supply current varies between two extreme values corresponding respectively to −15% and +15% of a nominal supply current.

4. The method of claim 1, wherein
step (iii) is carried out by bringing the gas sensor to different ambient temperature values;
step (iv) is carried out incorporating the measurements resulting from (iii) for each ambient temperature value so as to obtain a calibration function associated with each respective ambient temperature value.

5. The method of claim 1, wherein
step (iii) is carried out by bringing the gas sensor to different ambient temperature values;
step (iv) is carried out incorporating the measurements resulting from step (iii) for all of the ambient temperature values so as to obtain a calibration function that is common to all of the ambient temperature values.

6. The method of claim 1, wherein one parameter of the calibration function forms an exponent applied to the reference intensity, said parameter being estimated during step (iv).

7. The method of claim 6, wherein one parameter of the calibration function is a proportionality parameter (Z) defining a proportionality between:
the estimated intensity in the measurement spectral band in the absence of gaseous species; and
the reference intensity to which the exponent is applied, the proportionality parameter being estimated during step (iv).

8. The method of claim 1, wherein the calibration function comprises a ratio of a numerator over a denominator, such that
the numerator comprises a first multiplicative parameter applied to the reference intensity;
the denominator comprises a second multiplicative parameter applied to the reference intensity;
the first multiplicative parameter and the second multiplicative parameter are estimated during step (iv).

9. A method for measuring a quantity of a gaseous species present in a gas, the gaseous species absorbing light in an absorption spectral band, the method comprising:
a) placing the gas between a light source and a measurement photodetector, the light source being configured to emit an incident light beam, the incident light beam traveling through the gas toward the measurement photodetector, a supply electric current being passed through the light source so as to raise the light source to a temperature value;
b) illuminating the gas using the light source;
c) having the measurement photodetector measure a measured intensity of a light beam transmitted by the gas, in a measurement spectral band comprising the absorption spectral band;
d) having a reference photodetector measure a reference intensity of a reference light beam, the reference light beam being emitted by the light source in a reference spectral band;
steps b) to d) being carried out at a measurement instant, the method comprising, at each measurement instant:
e) from the reference intensity measured by the reference photodetector, incorporating a calibration function so as to estimate a light beam intensity that would be detected by the measurement photodetector in the measurement spectral band in the absence of gaseous species;
f) estimating a quantity of the gaseous species from the measured intensity measured during step c) of the intensity estimated during step e);
wherein the calibration function is established during a calibration phase, the calibration phase being performed by implementing steps (i) to (iv) of the method of claim 1.

10. The method of claim 9, wherein the calibration function is established in such a way that:
step (iii) is carried out by bringing the gas sensor to different values ambient temperature values;
step (iv) is carried out incorporating the measurements resulting from (iii) for each ambient temperature value so as to obtain a calibration function associated with each respective ambient temperature value;
step e) comprises:
estimating an ambient temperature, around the gas sensor;
selecting the calibration function as a function of the ambient temperature.

11. A gas sensor, configured to determine a concentration of a gaseous species in a gas, the gaseous species absorbing light in an absorption spectral band, the sensor comprising:
a chamber configured to contain the gas;
a light source, a measurement photodetector and a reference photodetector, the light source being configured to emit an incident light beam, the incident light beam traveling through the chamber toward the measurement photodetector and toward the reference photodetector;
wherein:
an electric supply current passes through the light source so as to raise the light source to a temperature value;
the measurement photodetector is designed to measure a measurement intensity of a light beam emitted by the light source, transmitted by the gas contained in the chamber, in a measurement spectral band comprising the absorption spectral band;
the reference photodetector is designed to measure a reference intensity of a reference light beam emitted by the light source in a reference spectral band;
the sensor comprises a processing unit, programmed to store a nonlinear calibration function established according to the method of claim 1 and to apply the calibration function to the reference intensity measured by the measurement photodetector.

12. The gas sensor as claimed in claim 11, comprising a temperature sensor, configured to measure an ambient temperature at the measurement instant, the processing unit being programmed to select the calibration function as a function of the ambient temperature from among a plurality of calibration functions respectively associated with different ambient temperatures.

* * * * *